United States Patent [19]

Czajka

[11] Patent Number: 4,605,414
[45] Date of Patent: Aug. 12, 1986

[54] RECONSTRUCTION OF A CRUCIATE LIGAMENT

[76] Inventor: John Czajka, One Executive Park Dr., Albany, N.Y. 12203

[21] Appl. No.: 617,742

[22] Filed: Jun. 6, 1984

[51] Int. Cl.⁴ .............................................. A61F 2/08
[52] U.S. Cl. ..................................... 623/13; 128/1 R; 128/92 B; 128/92 C; 623/16; 623/20
[58] Field of Search ................. 3/1 B, 1, 1.9–1.911; 128/92 B, 92 C, 1 R, 334 R

[56] References Cited

U.S. PATENT DOCUMENTS

| | | | |
|---|---|---|---|
| 3,545,008 | 12/1970 | Bader, Jr. ............. | 3/1 B |
| 3,797,047 | 3/1974 | Pillet ...................... | 3/1 B |
| 3,805,300 | 4/1974 | Tascon-Alonso et al. ... | 3/1 B |
| 3,953,896 | 5/1976 | Treace ................... | 3/1 B |
| 3,973,277 | 8/1976 | Semple et al. .......... | 3/1 B |
| 4,187,558 | 2/1980 | Dahlen et al. .......... | 3/1 B |
| 4,400,833 | 8/1983 | Kurland ................. | 3/1 B |
| 4,467,478 | 8/1984 | Jurgutis ................. | 3/1 B |

*Primary Examiner*—Ronald L. Frinks
*Attorney, Agent, or Firm*—Chapin, Neal & Dempsey

[57] ABSTRACT

In a process for surgically reconstructing the anterior cruciate ligament of the knee to restore its normal stability, the damaged ligament is removed and holes are formed in both the tibia and the femur. The holes extend through the knee joint with their adjacent ends terminating approximately at the points of origin of the removed ligament. A strip is partially severed from the patellar tendon, except at its lower end where it remains attached to the tibia. The tendon strip is shaped and sutured into a tubular configuration and fitted into an open-ended, tubular sleeve of Dacron open mesh fabric. The composite Dacron fabric and the tendon segment is inserted into the hole provided in the tibia, fitted through the knee joint and then advanced upwardly through the hole in the femur. The upper end of the composite insert is fastened in place by means of a bone member fitted into the upper end of the hole in the femur to wedge the upper end of the insert in fixed position.

5 Claims, 3 Drawing Figures

RECONSTRUCTION OF A CRUCIATE LIGAMENT

BACKGROUND OF THE INVENTION

The instability associated with anterior cruciate ligament rupture has created numerous problems and various possible solutions have been well documented in the literature.

U.S. Pat. No. 3,953,896, dated May 4, 1976, dislcoses a prosthetic ligament to be used to replace a damaged cruciate ligament. In this patent, the prosthetic ligament includes a cylindrical central portion of polyethylene and threaded outer portions provided with bushings to protect the central portion from abrasion caused by skeletal flexing. Fasteners, in the form of nut members, are also provided to fasten the prosthesis within the skeletal apertures.

U.S. Pat. No. 3,545,008, dated May 27, 1968, also discloses a tendon prosthesis which consists of a Dacron mesh sleeve sutured to the proximal ends of a ruptured tendon. The sleeve includes a mesh netting at its outer ends to encourage fibroblastic infiltration to occur between the severed ends of the tendon for anchoring the prosthesis to the tendon.

U.S. Pat. No. 4,187,558, dated Feb. 12, 1980, relates to a prosthetic ligament positioned within a surgically prepared passageway in the bone, and a Dacron and/or Dacron and silicone strand is disclosed as a replacement for a cruciate ligament with Dacron velour fabric used as collars at the outer ends of the central portion to promote new tissue growth.

U.S. Pat. No. 3,797,047, dated Mar. 19, 1974, discloses an artificial tendon material which consists of a tubular sheath of silicone elastomer with an inner tensile element of knitted fabric.

U.S. Pat. No. 3,805,300, dated Apr. 23, 1974, teaches a tendon which is composed of a cord-like combination of silicone and Dacron strip with transverse openings for the natural tendon to be woven therethrough.

In these prior art procedures, the damaged natural tendon is relaced with a synthetic member which is a biocompatible material, usually Dacron and/or silicone. One problem with these techniques is that the tendon prosthesis is essentially synthetic, except that some means is utilized to encourage functional anastomosis. For example: in the Bader U.S. Pat. No. 3,545,008, mesh flaps are sutured to the ends of the ruptured tendon and in the Alonso U.S. Pat. No. 3,805,300, the resected tendon is inter-woven through perforations in the synthetic cord member.

The present invention involves the replacement of a cruciate ligament with a composite synthetic and biological structure to provide maximum mechanical and structural stability, both short and long-term, after surgical reconstruction.

The principal object of this invention is to provide an improved method of surgically reconstructing a severely damaged or ruptured tendon.

Another object of this invention is to provide for ligament augmentation particularly adapted to the anterior cruciate ligament.

The above and other objects and advantages of this invention will be more readily apparent from the following description read in conjunction with the accompanying drawing in which.

Figure 1:
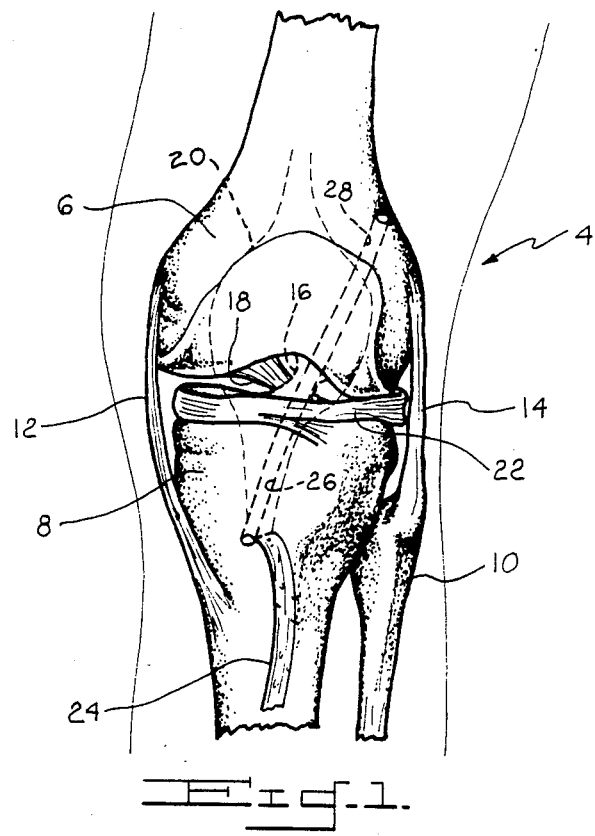
FIG. 1 is a front elevational view of a knee joint in which a ruptured anterior cruciate ligament is to be surgically reconstructed in accordance with this invention.

Referring now in detail to the drawings, in FIG. 1 is shown an injured knee joint 4 being surgically prepared for anterior cruciate ligament reconstruction. The femur and tibia are represented at 6 and 8, respectively, and the fibula at 10. The medial collateral ligament and lateral collateral ligament are shown at 12 and 14. The anterior cruciate ligament is illustrated in broken line construction at 16 and the posterior cruciate ligament at 18. These ligaments are the primary ligaments which stabilize the knee joint and they extend diagonally at approximately right angles to each other and, hence, are referred to by the adjective "cruciate." The knee cap or patella is shown at 20 in FIG. 2 and in phantom in FIG. 1. The meniscus is illustrated at 22.

In the event of a torn or ruptured anterior cruciate ligament, serious knee joint instability invariably results and the prior art, as discussed above, discloses various techniques for attempting satisfactory restoration of normal knee joint stability. In accordance with my invention, the anterior cruciate ligament is replaced or reconstructed with a ligament augmentation composite in the following manner.

Figures 2, 3:
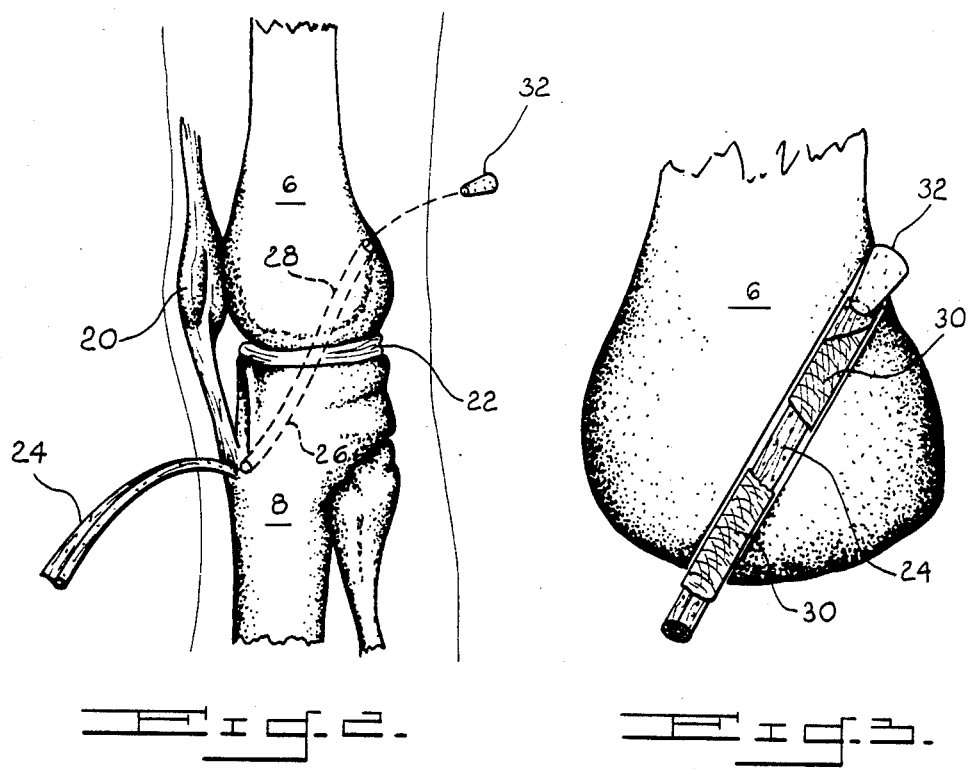
FIG. 2 is a side elevational view of the knee joint shown in FIG. 1.
FIG. 3 is an enlarged cross-sectional view illustrating a ligament augmentation composite used in the process embodying this invention.

The ruptured anterior cruciate ligament 16, shown in phantom, is first surgically removed and a strip 24 of tendon tissue is severed from the quadriceps mechanism, in particular the patella tendon, leaving it attached to the tibia at its lower end, as best illustrated in FIG. 2. The tissue for this strip is available in the inferior expanse of the quadriceps mechanism, and especially from that portion of the patellar tendon overlying the patella. A hole, channel or bore 26 is then drilled diagonally through the tibia, starting from a point adjacent the attached end of the strip 24 and terminating at approximately the same location as the point of connection of the cruciate ligament 16 to the tibia. A second hole, bore or channel 28 is drilled diagonally through the femoral condyle to approximately the point of connection of the ligament 16 to the femur. The holes 26 and 28 are drilled to be approximately in axial alignment along the same general line as that of the removed anterior cruciate ligament.

The tendon strip 24 is then shaped and sutured into a tubular cross-sectional form, using absorbable suture material. This tubular tendon is next fitted within a unitary, seamless Dacron (polyethylene glycol terephthalate) mesh sleeve or sheath 30 (FIG. 3) about 8-12 mm in length and about 1 cm in cross-section, or approximately the same dimensions as the anterior cruciate ligament of the human knee. Some suturing may also be used to consolidate the inner biological segment and the outer synthetic component of the composite reconstructed ligament.

Whenever feasible, this composite structure is further sheathed with the synovium membrane within the femoral intercondylar notch and infrapatellar fat pad. This is also accomplished by using absorbable suture material in order to make this composite member as similar as possible to the human anatomic anterior cruciate ligament, which has a synovial covering.

The composite sleeve and tendon is then fitted upwardly through the hole 26 in the tibia and the hole 28 in the femur until its terminal or free end is positioned at or near the outer end of hole 28, as best illustrated in FIG. 3, in which a central portion of the sleeve 30 is shown broken away. A plug or wedge 32 of bone, which is preferably removed surgically from the femoral condyle at the site through which the hole 28 is to be drilled, is used to fasten or secure the upper end of the reconstructed ligament in place within the bore 28. This is done by firmly wedging the upper end of the composite against the wall of the bore 28 with the bone plug 32, as illustrated in FIG. 3.

The tubular composite structure, such as described above, is considered superior in both its mechanical strength and as a template to encourage fibroblastic ingrowth and ultimate longitudinal alignment of collagen fibers. The intraluminal tendonous segment 24 thus not only increases the overall strength of prosthesis but also increases fibrous ingrowth and maturation.

Having thus described the invention, what is claimed is:

1. Process for surgically reconstructing the anterior cruciate ligament of the knee joint comprising the steps of forming aligned holes through both the tibia and the femur towards the points of origin of the damaged ligament, removing the damaged ligament and substituting a composite graft therefor by severing a strip of the patellar tendon, then fitting the same into an open-ended sleeve of synthetic biocompatible material, fitting the two-ply composite structure within the aligned holes formed in the tibia and femur and using a fastening means to secure the free end of the composite structure in place within the femur.

2. Process for surgically reconstructing a ligament as set forth in claim 1, in which the tendon strip is shaped and sutured into tubular form using an absorbable suturing material.

3. Process for surgically reconstructing a ligament as set forth in claim 2, in which the sleeve is an open weave polyethylene glycol terephthalate fabric tube about equal in length to the tendonous inner segment.

4. Process for surgically reconstructing a ligament as set forth in claim 3, in which said fastening means comprises a tapered plug of human bone removed from the patient's knee joint at the point or origin of one of said aligned holes.

5. Process for surgically reconstructing a ligament as set forth in claim 4, in which the portion of the polyethylene glycol terephthalate sleeve which spans the joint between the tibia and the femur is sheathed within the sonovial membrane and sutured thereabout by absorbable suturing material.

* * * * *